United States Patent [19]

Hawkins et al.

[11] Patent Number: 4,898,182
[45] Date of Patent: Feb. 6, 1990

[54] APPARATUS FOR EVALUATING HEART FITNESS

[76] Inventors: Brian Hawkins, 8 MacDonald Ave.; Jerald Greenberg, 34 Maple Ave.; Ofer Alon, 6 MacDonald Ave., all of Armonk, N.Y. 10504; Victor Marten, 144-45, 41 Ave., Apt. 3S, Flushing, N.Y. 11355; Edward Banyai, 133 Woodland Ave., New Rochelle, N.Y. 10805; Jennifer A. Edwards, 8 MacDonald Ave., Armonk, N.Y. 10504; David M. Banyai, 133 Woodland Ave., New Rochelle, N.Y. 10805; Juan C. Sanchez; Eran Sitnik, both of 137 Old Kisco Rd., Armonk, N.Y. 10504; Joseph A. Yozzo, 17 Lawrence St., Mt. Kisco, N.Y. 10549

[21] Appl. No.: 152,113
[22] Filed: Feb. 4, 1988
[51] Int. Cl.$^4$ .............................................. A61B 5/04
[52] U.S. Cl. .................................. 128/707; 128/709; 128/696
[58] Field of Search ............... 128/707, 709, 695, 696; 272/69

[56] References Cited

U.S. PATENT DOCUMENTS

| | | | |
|---|---|---|---|
| 3,518,985 | 7/1970 | Quinton | 128/707 |
| 3,675,640 | 7/1972 | Gatts | 128/671 |
| 4,278,095 | 7/1981 | Lapeyre | 272/69 |
| 4,281,663 | 8/1981 | Pringle | 128/689 |
| 4,319,581 | 3/1982 | Cutter | 128/707 |
| 4,367,752 | 1/1983 | Jimenez et al. | 128/707 |
| 4,566,461 | 1/1986 | Lubell et al. | 128/707 |
| 4,708,337 | 11/1987 | Shyu | 272/69 |

OTHER PUBLICATIONS

Biosig, Inc., INSTA-PULSE heart rate monitor sales brochure, Print date 9/78, BioSig Inc., P.O. Box 651, NDG, Montreal, Quebec, H4A 3R1, Canada.

Primary Examiner—Francis Jaworski
Assistant Examiner—George Manuel
Attorney, Agent, or Firm—Stephen E. Feldman

[57] ABSTRACT

A heart fitness evaluation system is set up in booth form in which a participating person may have the fitness condition of his heart evaluated based on a step test protocol. Personalized data is transmitted to the system in the form of selected answers to questions proposed, and the person is classified according to such data provided for the purposes of data comparison. The person engages in supervised exercise over a timed period to accelerate heart functions. After the activity, the person's heart is monitored to determine the recovery rate of the heart over real time. Comparison of the recovery rate is made against stored physiological data relating to heart rate recovery of classified persons, which is translated in to the fitness level of the person's heart and displaying such results.

10 Claims, 4 Drawing Sheets

APPARATUS FOR EVALUATING HEART FITNESS

BACKGROUND OF THE INVENTION (1) Field of the Invention

This invention relates to a method and apparatus for evaluating the beat rate of the person's heart after having the person engage in supervised exercise. More particularly the present invention relates to an apparatus which may be a coin-operated booth type apparatus for evaluating the condition of a person's heart based on selected personal data provided by the person tested and the monitored reaction of the heart of the person prior to and after supervised exercise.

(2) History of the Invention

For years now, individuals have gone to medical authority and have exposed themselves to electro-cardiogram devices (EKG) which have provided a readout in an analog strip of the characteristics of the person's heart beat. The EKG readout is normally interpreted by a doctor who diagnosis the condition of the person's heart based on what doctors believe to be normal or healthy heart beat under relaxed conditions.

The EKG machine is a medically accepted tool that detects the electric impulses of the heart through the use of electrodes electrically coupled to selected parts of the chest. The detected impulses are converted to an analog read out which, in the medical profession are normally used in evaluating the condition of the person's heart. In operating an EKG, machine electrodes are positioned on the body of the person being tested which electrodes detect the electric impulses of the heart while the person is totally relaxed.

EKG machines have also been used to monitor a person's heart during supervised exercise, such as while a person exercises on a treadmill, for example. These are usually referred to as stress tests.

More recently other electrodes have been developed to sense and detect heart action. One example is found in U.S. Pat. No. 3,702,113 which discloses an electrode apparatus mounted on the handlebar of a exercise machine which, when grasped by the hand, sense signals which have characteristics which correspond to the functioning of the heart.

PRESENT INVENTION

Summary of the Invention

The present invention is an heart fitness evaluation apparatus which is distinguishable from the normal EKG test apparatus and routine where a person being tested is in fully relaxed state and is distinguishable from the normal stress test apparatus and routine where a person is monitored with EKG apparatus during supervised exercise. In the concept of the present invention heart fitness evaluation apparatus, which may be a coin-operated apparatus, follows a step test protocol by first engaging in a question and answer routine in order to obtain and use personal data of the person to be tested to classify the person for physiological data comparison. Instructions are provided to perform a step test exercise under monitored conditions. The heart reactions are thereafter checked on a timed basis to determine the recovery heart beat rate. The recovery rate is compared with predetermined physiological recovery rate data for persons in a classification common to the person being tested. The comparison is translated in heart fitness evaluation.

In its preferred embodiment, as will be described below, communication between the apparatus and the person using the apparatus is done audio visually, by use of a cathode ray tube (CRT) or monitor using written or printed language and/or meaningful pictures, signs and/or cartoons. This type of communication is preferred because of the cost involved and the ruggedness of the equipment, some of which will be exposed to the public. However, audio communication between the machine and person using the machine may be accomplished using known technology with relatively minor changes and/or additions to the equipment as disclosed.

As respects the apparatus of the invention, the apparatus is translated into a machine system which is computer controlled and responsive to a program which may take any one of several forms. The program is used to establish the machine routine; isolate characteristics of the person being tested; keep the testing or monitored activity within established limits and compare the detected data against programmed, established data and provide a readout characterizing the condition of the heart.

Objects of the Invention

It is an object of the invention to provide a booth type heart condition evaluation machine.

Another object is to provide a coin-accept, heart beat rate sensing and evaluating machine.

A further object is to provide a booth type programmed computer apparatus for monitoring and determining the condition of the heart based on personal data of the person, supervised exercise of such person and comparison of the heart functions after exercise against established physiological data.

A still further object of the invention is to provide a coin-accept, booth type condition determining machine for monitoring and determining the condition of the heart.

DETAILED DESCRIPTION OF THE PREFERRED EMBODIMENT

Figure 1:
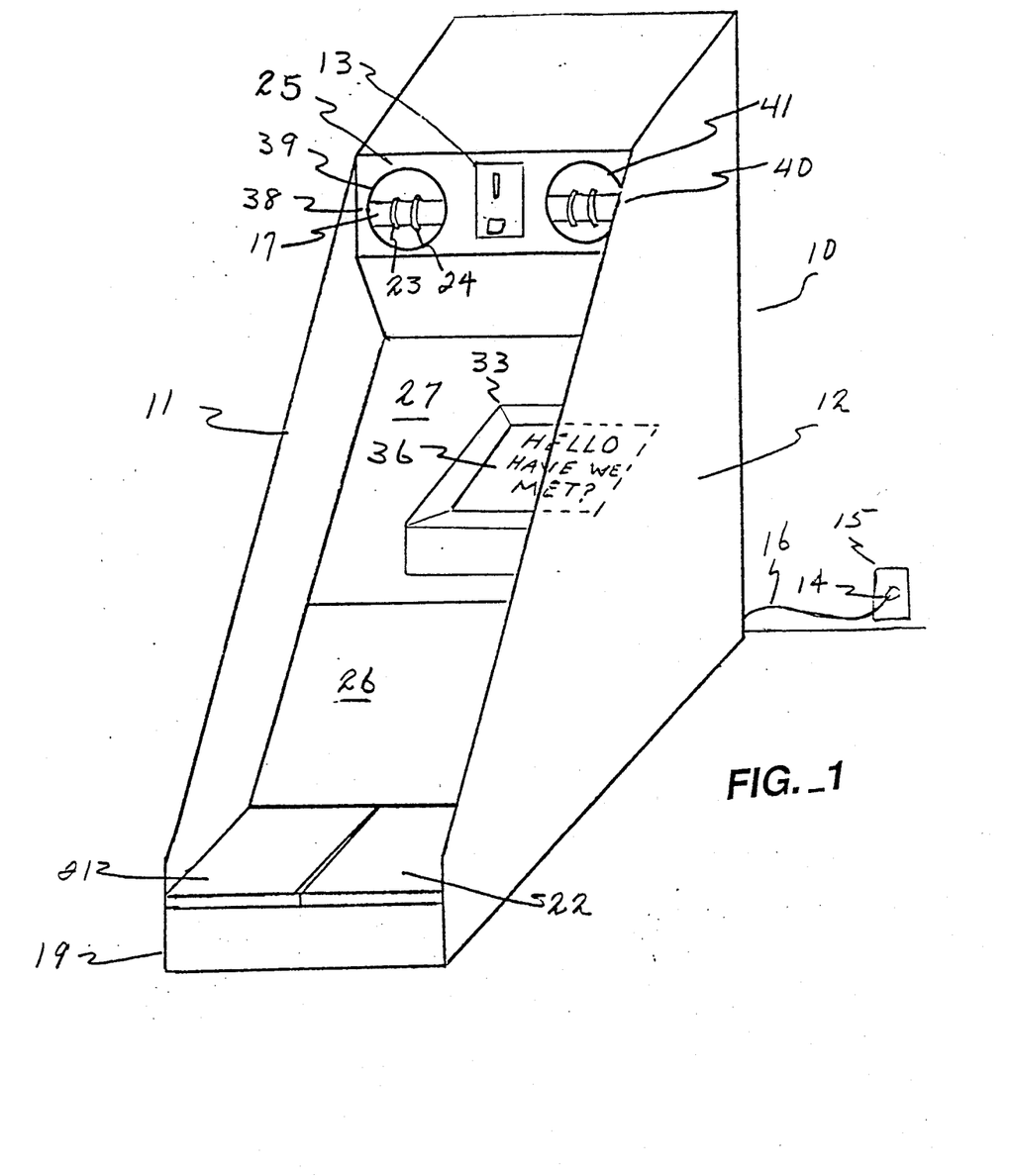
FIG. 1 is a pictorial representation of the booth-type apparatus of the present invention.

FIG. 1 illustrates in a pictorial perspective view a booth type coin-accept step test or heart fitness evaluation machine. The cabinet 10 is shown with protective sides 11 and 12 isolating the interior and forming a booth. The system supported in the booth is operated by electric power represented by the plug 14 and the wall outlet 15. The line 16 conducts electric power to the apparatus. The coin slot/return 13 receives coins which are sensed, when received and effectively actuate operation of the read-out capability of the apparatus.

It will be noted that similar components are identically numbered throughout the drawings.

The cabinet 10 sits on a base 19 which, in the front thereof supports a two-step treadle 21 and 22. The height at which the surface of the dual treadle is above the floor approximates the height of a normal step that is, approximately 8 inches. The height between the floor and the top surface of the dual treadle as suggested in the preferred embodiment is not critical and may vary, however, as will be clearly brought out below the dual treadle features in the exercise to be performed and height of the steps in the step-up, step-down routine, to be performed in the exercise portion of the test is a factor considered when calculating the amount of work performed by the person taking the test. Thus, the height of the treadle surface over the floor is a factor that is used in calculating the physical work performed and the time of performance by the person being tested.

It will be noted that the two-piece treadle is set up in left-side, right-side arrangement. This is so arranged so that when instructed, the person under test can step up and down with right foot and left foot under close electronic supervision, and in a rhythm or pace determined by the program and for a time determined by the program so as to put the desired working stress on the heart so as to accelerate the heart beat rate.

The interior of the booth 10 includes an upper panel 25 with holes 39 and 41 exposing electrodes 38 and 40, respectively. The panel 25 also supports the coin slot 13 used in conjunction with the read-out. In using the invention in some environments it may be desired to eliminate the coin-sensing feature and permit free operation of the apparatus.

Figure 2:
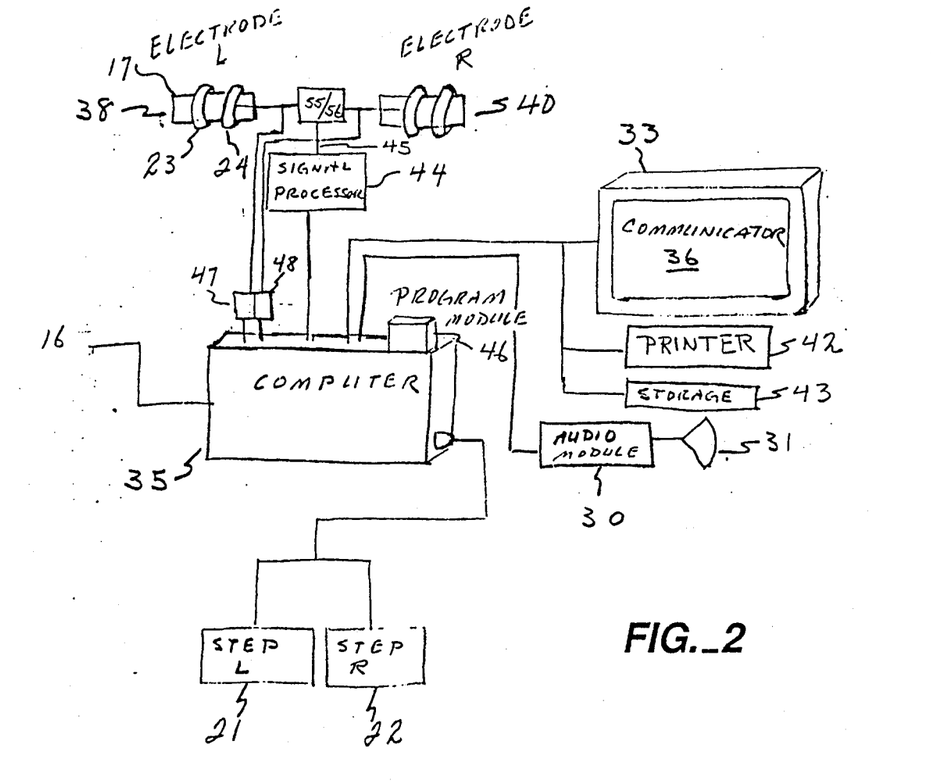
FIG. 2 is a block diagram of a preferred system usable in a coin-accept, booth-type apparatus.

The holes 39 and 41 are used to provide convenient access to sound produced by stereo speakers mounted behind the panel 25. Such audio speakers are represented in FIG. 2 at 31, being part of an audio module 30 forming a sound system. The sound system is integrated into the overall machine system and on command of the computer provides a rhythmic beat or tune which is played in order to help the person performing the exercise keep performance at a predetermined pace during the exercise portion of the routine. If verbal communication between the machine and the person being tested is desired, the capability of the audio module can be expanded by adding a voice synthesizer and a microphone with a speech analyzer so that two-way voice communication between the machine and the person being tested can be conducted.

However, in the preferred system the audio module includes a selection of rhythmic beats or tunes so as to influence the timing or pace of the exercise performed by the person being tested, according to the relative value of the characteristics or factors of the person being tested.

It has been found that the audio module can be used as a mechanical barker, to call attention to the machine and to verbalize instructions to the person under test.

The plate 27 is a clear panel preferably covering a finished interior Behind the clear panel 27, is a communicator 33, which is preferably a cathode ray tube (CRT) or television monitor, (without the antenna and channel distinguishing apparatus) which is driven by the computer 35, as controlled by a program module 46 inserted into the computer, as seen in FIG. 2.

The communicator screen 36 may be used to convey instructions and to ask questions for obtaining personal data or factors relative to the person to be tested. A key board (not shown) can be connected to the computer, and this could serve as an answering medium for the person to be tested, for the questions appearing on the screen 36. The use of script graphics, where one writes electronically or otherwise on the screen of a CRT, for a vehicle of communication has also been anticipated, and may be used, if desired.

In the preferred arrangement when a question appears on the screen 36 a sequence of answers also appears and a selected answer is acknowledged by the person to be tested by grasping one of the electrodes 38 and 40 located in the upper part of the cabinet 10.

Access to the electrodes is through holes in the upper face of the cabinet. The hole 39 providing access to electrode 38 and hole 41 providing access to electrode 40.

Figure 3:
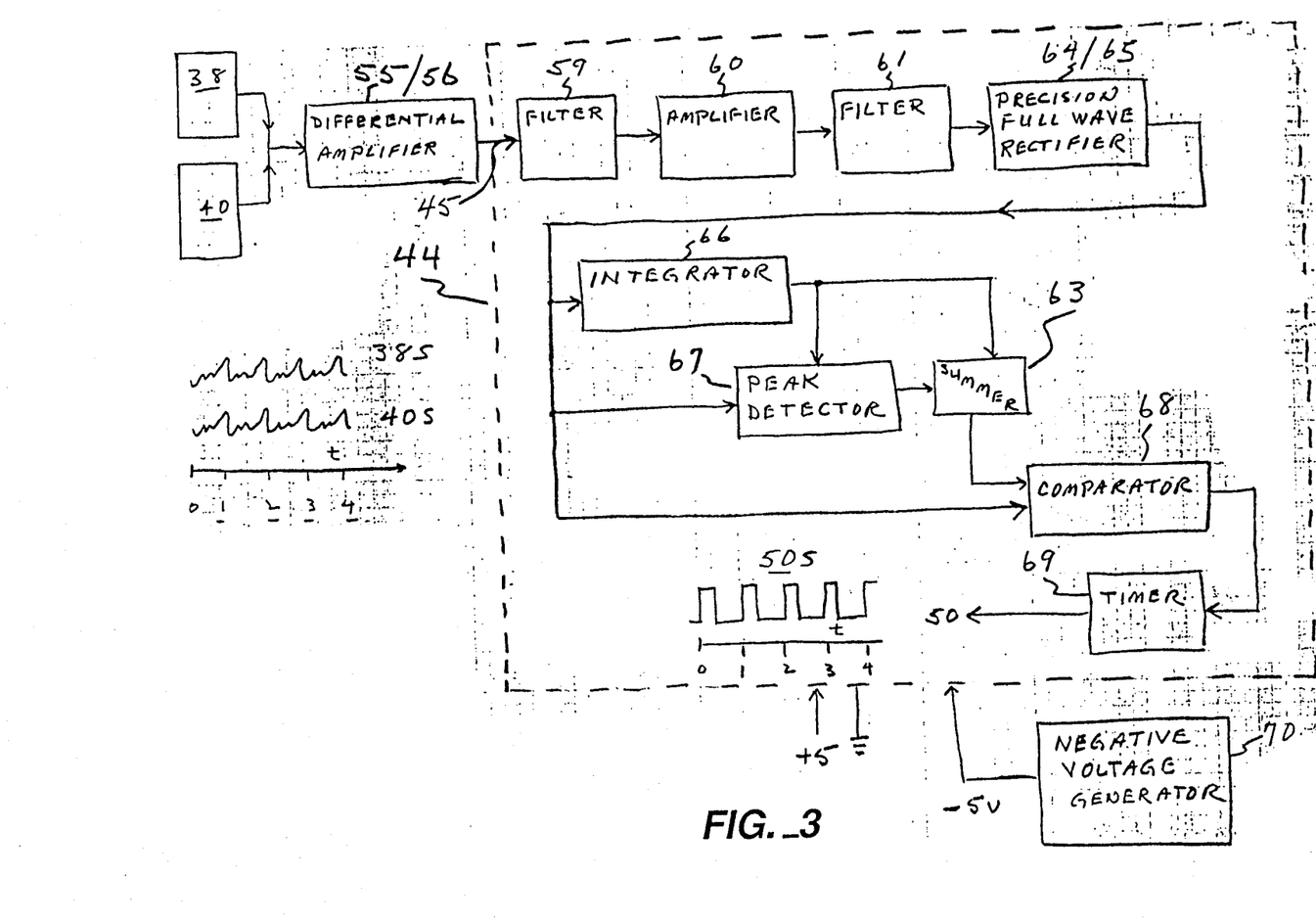
FIG. 3 is a block diagram of a signal processing circuit.

Each electrode 38 and 40 is in the form of a bar 17 which supports spaced electrode rings 23 and 24 (shown and called out on electrode 38). When both electrodes 38 and 40 are grasped by the hands of a person such that both the rings 23 and 24 are contacted by the same hand, (with the corresponding rings on electrode 40 also contacted by the other hand) dual signals, such as represented as 38S and 40S in FIG. 3, are applied to the differential amplifier 55/56. The output of the differential amplifier is an anolog signal at 45 which represents the electrical signals from the heart of the person grasping both electrodes. The analog signal 45 is applied to the signal processor 44 for processing and conversion. The signals applied to the differential amplifier are represented as 38S and 40S.

When only one of the electrodes 38 or 40 is grasped by the hand of a person, the electrode so grasped functions as a digital switch. Since only one signal 38S or 40S is applied to the differential amplifier the section 56 of differential amplifier 55/56 does not function. (see FIG. 4) Thus no signal is passed to the signal processor 44. The signal from the grasped electrode is applied to the integrated circuit either 47 or 48, depending upon which electrode is grasped. The integrated circuit so driven provides a pulse output at 47S or 48S which is digital in form. This digital pulse may be used as a logic pulse for indicating selection of an answer to a question, as discussed below.

The electrodes are preferably located at an upper position at approximately chest level of the average man when standing on the two-part treadle. This location or some comparable location is preferred in order to discourage grasping on to the electrodes during the exercise portion of the routine. Other locations may be used if desired, but the location of the electrodes should be readily available to the person being tested. They should be located so that the person being tested should preferably be standing in a natural stance position when grasping the electrodes.

Directing attention to FIG. 2 a block diagram of the heart fitness evaluation system is presented. The steps 21 and 22 are represented as connected to a computer 35. The computer may be an off-the-shelf personal computer, such as a COMMODORE 64/128; IBM; APPLE or any other personal computer or other apparatus designed to accomplish substantially the same purpose. The computer may be located in the cabinet 10 behind the panel 26, in a secure compartment.

The treadle steps 21 and 22 represent the left and right treadle steps respectively which are connected to an input to the computer 35. The steps provide distinguishable signals to the computer. The electrodes 38 and 40 are represented as connected to a differential amplifier 55/56, the output, 45, of which is connected to a signal processor 44. Each dual ring electrode is also connected to an integrated circuit chip 47 and 48 respectively which provides a pulse, in digital form when connection between the two electrode rings of an electrode is made, by grasping the electrode with one's hand, as discussed above.

As will be more fully described below, when both the electrodes 38 and 40 are grasped by the hands of a person, (one electrode grasped by each hand) analog signals representing the functions of the heart of the person grasping the electrodes are applied to a differential amplifier that is designed to respond to dual inputs to have an output that represents the dual inputs and has characterstics of the dual input signals. The output 45 is applied to a signal processor 44 which receives the analog signals which represent the functions of the heart of the person grasping both electrodes. As seen in FIG. 3, analog signals 38S and 40S which represent the heart functions are processed into a digital signal 50S which is provided at an output 50. The digital signal 50S, which represents the heart beat rate, is applied as an input to the computer, which is preferably a digital instrument.

The computer 35, under the control of the program in the program module 46 follows a pre-set routine, first obtaining information personal to the person to be tested so that the individual can be categorized or classified. The protocol for the preferred step test calls for the use of the age and the sex of the person for classification. After receiving the personal data for person classification, the routine calls for supervising the person in predetermined activity or exercise for a predetermined time. When the exercise is finished, the person is instructed to grasp both electrodes with his hands and hold the electrodes until told to release them. During this time interval the computer calculates the heart beat recovery rate (the heart beat rate having been accelerated as a function of the exercise performed) and compares the recovery rate with predetermined recovery rate data based on physiologically established recovery rate data for persons falling in the same classification as the person tested. The comparison is translated into an evaluation of heart fitness.

In operation, the program starts from the beginning of the routine. Questions appear on the screen of the communicator along with a selection of answers, with instructions on what to do in order to answer the question.

By way of example, questions, answers and instructions may take the following form:
Are you a man or a woman?
If a man grasp one electrode now
WAIT
If a woman grasp one electrode now
WAIT
Please release electrodes now
How old are you?
Younger than 12 years grasp one electrode now
WAIT
13–18 grasp one electrode now
WAIT
19–30 grasp one electrode now
WAIT
31–40 grasp one electrode now
WAIT
41–50 grasp one electrode now
WAIT
51–60 grasp one electrode now
WAIT
61–66 grasp one electrode now
WAIT
67–72 grasp one electrode now
WAIT
Over 72 grasp one electrode now
WAIT
please release electrodes When one grasps one of the electrodes to answer the question of age, for example, further questioning of age is cut off after the WAIT period and the person is instructed to release the electrodes. If there is another question in the routine depending on the protocol of the step test used, the next question is addressed. It will be appreciated that a program can be written which partitions the various personal characteristics into any group of ranges desired. It should also be noted that the present partitioning into groups or ranges of the personal characteristics of the person to be tested are examples of partitions that may be used. Obviously the memory bank in the program may be partitioned into similar groups so that the person to be tested is properly classified or catergorized so that the recovery rate of the heart of the person tested can be matched with or compared with predetermined heart recovery rates in the proper classification of persons for providing an evaluation of heart fitness.

In accordance with the answers provided through these communications, which two-way communication may take other forms such as punching or pressing selected keys on a key pad provided for the same; audio communication between the machine and the person to be tested; script and/or graphics through electronic writing or making out a punch or data card and inserting the card into a slot so that the machine can read the card, the person to be tested is classified or categorized. One or more, or a combination of these and other methods of communication between the person to be tested and the machine may be used.

In some cases, as dictated by the protocol of the step test used, additional personal data of the person to be tested may be required for more particularly classifying the person. The personal factors of weight and/or height of the person to be tested are examples of factors that may be considered. If additional data is required for adherence to step test protocol, answers to questions relating to the required data may be obtained using the same techniques as used for obtaining data on the factors of age and gender.

If data on the personal characteristic of weight is to be considered, it may be desired to integrate a scale in the system that automatically weighs the person when such person steps on both steps of the dual step treadle. The weight data may be translated into electric signals which are applied to the computer for use in classification.

If height data is to be considered in classification, it may be desired to obtain height data by using mechanical and/or electronic means. An extendable measuring rod may be used in order to measure the height of the person. Extension of the measuring rod representing the height measured may be translated into electric signals which are applied to the computer.

Electronically, electro-magnetic waves or sonic waves may be used to measure the height of a person, by reflecting radiated wave signals off the head of the person whose height is to be measured. The travel time of the return signal may be translated into height of the person and applied to the computer.

Data on the factors of height and/or weight may also be provided to read-out or print-out in accordance with the capability of the system.

In the preferred routine, after the machine has received the information for classifying the person to be tested, instructions are given for the person to stand on the treadle steps and grasp each of the electrodes, one by each hand, and hold in relaxed position. During this interval the relaxed rate of the person's heart is monitored and sensed, and the pulse rate of the person appears on the screen. This data, however, is not used in the step test protocol used in the preferred embodiment of the invention. However, other step test protocols may call for and use the normal pulse rate of the person tested in computation of heart fitness.

After having received the data requested, the person is instructed to release his grip on the electrodes and step down from the treadles. Instructions are then provided to step up, with right foot and left foot and step down with right foot and left foot and repeat the process in rhythm, until instructed to stop. This is the step test exercise particularly designed to accelerate the beat rate of the heart of the person performing such exercise. During the step-up and step-down routine the pace at which the exercise is performed is monitored and instructions are transmitted to speed up, if too slow, or to slow down, if too fast. At the end of the timed exercise routine the person is instructed to stand on the treadles and grasp and hold both the electrodes with his hands, respectively. This is to be done for a timed period.

During a timed interval following the exercise routine which has caused the heart to beat at an accelerated rate, the recovery rate of the heart of the person tested is determined. In the preferred routine the beat of the person's heart is monitored over a timed interval of sixty (60) seconds immediately following completion of the exercise routine. During the last thirty (30) seconds of the sixty (60) second interval following completion of the exercise routine the recovery rate of the heart is determined. The recovery rate so determined is compared with recovery rates for persons in the same category or class as the person tested and previously classified, and this comparison is translated into heart fitness.

It will be appreciated that in order to accomplish the objectives of the invention a program must be written to control the computer and direct operations of the computer during the routine. The program is stored in the program module. Also stored in the program module is data representing the comparison scale or criterion of physiologically established data against which the determined recovery rate is compared.

As previously mentioned, the heart beat signal, when sensed by the hand-grasped electrode is an analog signal, such as represented as 38S and 40S in FIG. 3. It will also be appreciated that when the computer used is a digital instrument the signal input acceptable to the computer should be digital in form. Thus, the analog signal representations of the heart beat are converted into digital signals which correspond characteristically to the analog signals.

Figures 4, 4A:
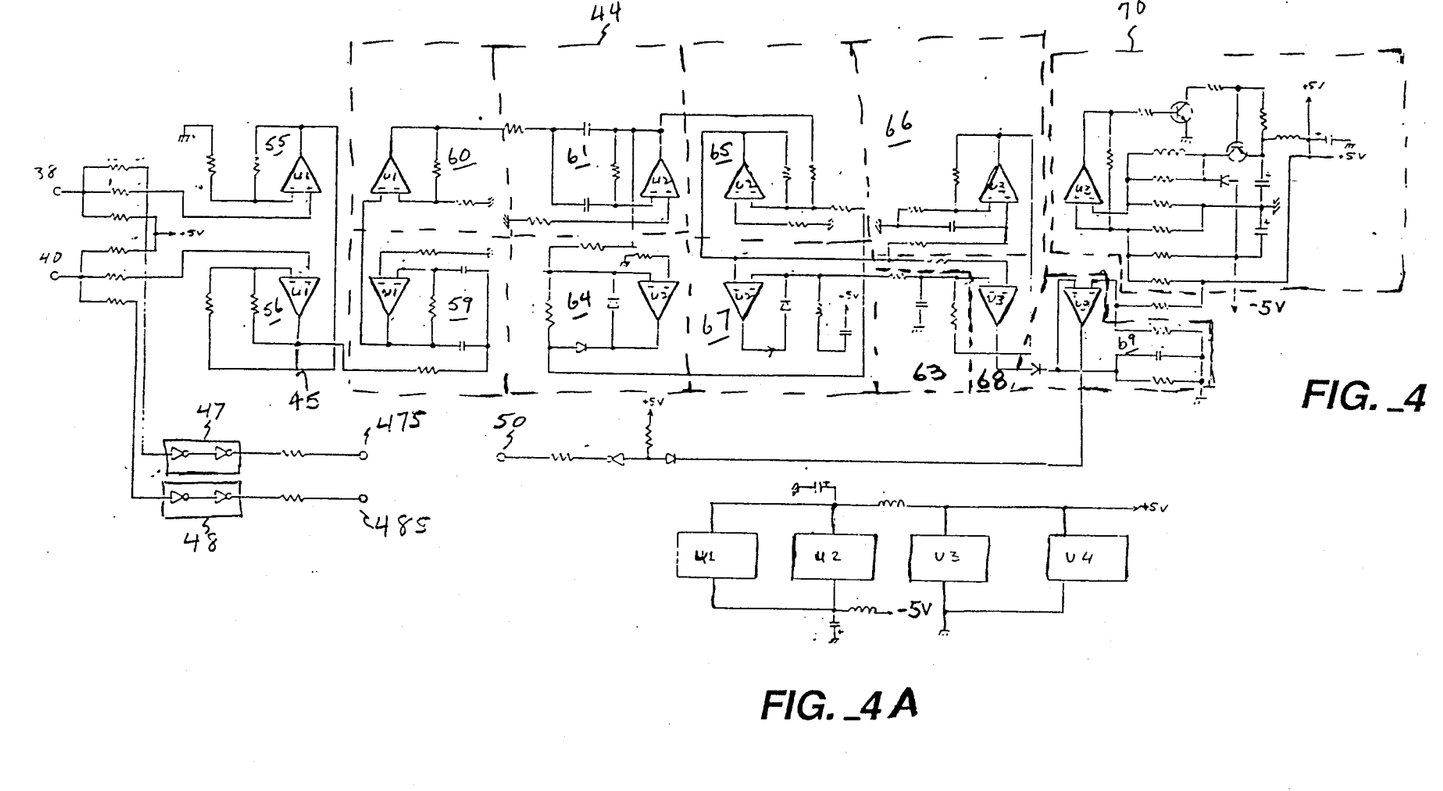
FIG. 4 is a circuit diagram of a preferred embodiment of signal processor.
FIG. 4a is a diagram of the power connections.
Figure 4:
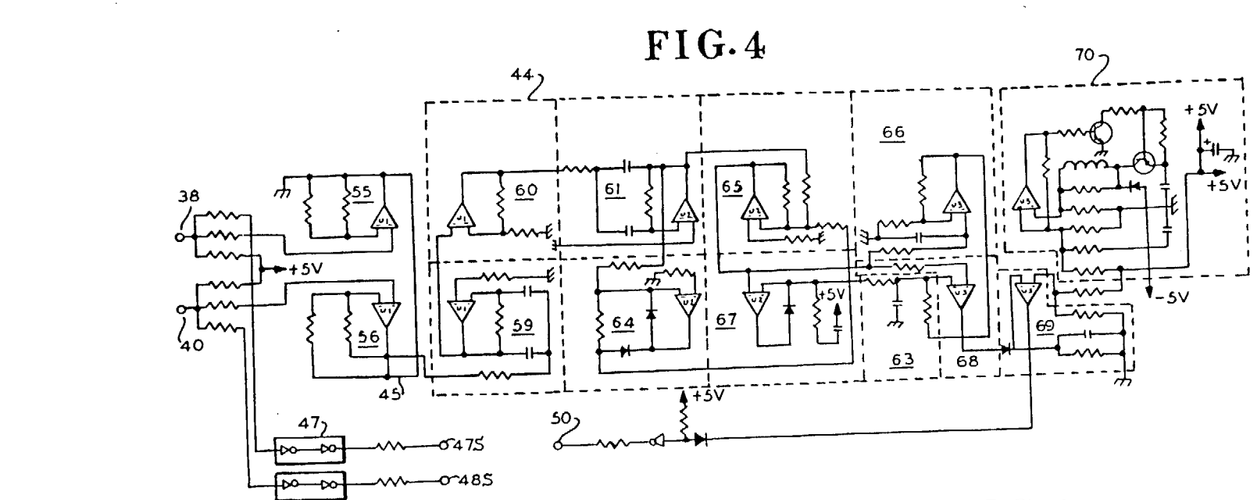
Figure 4A:
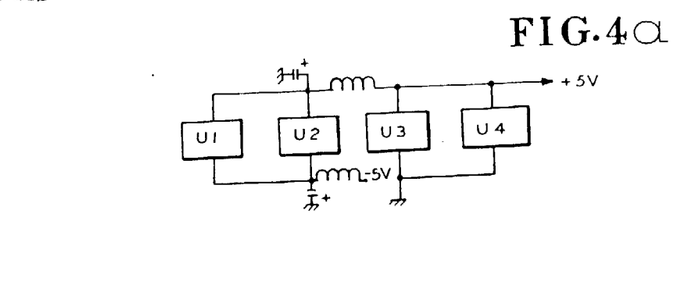

The block diagram in FIG. 3 represents a preferred analog to digital (A to D) signal converter, the circuit of which is represented in schematic form in FIG. 4.

Referring to FIGS. 3 and 4, the electrodes 38 and 40, when grasped by both hands, sense electric impulses which are analog in nature and include characteristics of heart functions. These signals are represented at 38S and 40S. The analog signals are fed to differential amplifier 55/56, and the output at 45 is applied to the signal processor 44.

The analog signal is fed to a band pass filter 59 and thence to an amplifier 60. The signal is again filtered in filter 61 and fed to a precision full wave rectifier 64/65.

The rectified signal is applied to an integrator 66, a peak detector 67 and to a comparator 68. The output of integrator 66 is applied to the peak detector 67 as a recovery control input and to a summing circuit 63. The output of the peak detector 67 is also applied to the summing circuit 63.

The output of the summing circuit 63 is applied, along with the rectified signal, to the comparator 68. The output of the comparator is applied to a timer 69. The output of the timer 69 is at 50 and is a series of digital pulses, such as shown at 50S, the pulse front edges of which correspond in real time to the beat rate of the heart.

The digital signal 50 is applied to the computer (see FIG. 2) as an input representing heart beat rate in real time.

Also represented in FIG. 3 in block form and in FIG. 4 in schematic form is a negative voltage generator 70.

The components of the signal processor function at a level of voltage of $+5$ volts to $-5$ volts. The $+5$ volts to 0 volts is obtained by a rectifier, not shown. However, the negative voltage, that is 0 volts to $-5$ volts is provided by the negative voltage generator 70. FIG. 4a represents, in block form, how the voltages are applied to the integrated circuit components.

Although the preferred embodiment of the heart fitness evaluating system is arranged in a booth, it is apparent that the system may be embodied in other forms.

A suggested technique for a pay machine is to have the system of the machine stand ready to be operated when not in use, without the need to pay for initiating operation of the machine. The coin operated switch may be made to function in conjunction with the read-out and/or printout.

Returning to FIG. 2 it will be noted that a printer 42 and a storage module 43 are connected to the output of the computer 35. The printer may be used to provide a hard copy or print out of the heart fitness data. Such data may also be stored in the storage module 43 which may include retrieval capability.

In addition, a key board may be provided as part of the printer or the storage module so that other data, such as name, address and/or date, or any other data may be inserted into the computer along with the classification data and heart fitness data. The key board, (not shown), printer and storage module may take the form of a second computer working in conjunction with the main computer 35. These various equipment may be located external to the cabinet, if desired.

The storage module may be used to store heart fitness results and other data for later retrieval and use. Retrieved fitness data may be used by individuals in comparing workout usefulness and/or workout statistics. This may be desired for heart fitness systems used in fitness centers and for home systems. A print out of fitness results may include personal identification, dated prior fitness data and dated present fitness data, and any other data entered and stored in the storage module under the personal identification. Personal identification may be in the form of a name and/or code number.

Although dual steps, in a common plane, are disclosed for providing electronically supervised exercise, other exercise devices may be used, as dictated by the protocol of the heart fitness evaluation test used.

It is apparent that a program must be written for control of the computer. Once the concept of the heart fitness evaluation apparatus is established and taught, the generation of a program for control of the computer becomes a matter of writing the same. The data in the memory bank against which the monitored characteristics may be measured or compared for evaluating the fitness of the heart may be medical data or physiologically established data of heart beat recovery rates for persons having different heart fitness ratings respectively for each classification of person.

Thus, there has been shown and described a novel concept and apparatus for evaluating fitness of the heart of a person by classifying the person to be tested, according to information provided by the person; instructing the person to be tested in a exercise routine; having the person engage in supervised exercise and monitoring the heart characteristics of such person immediately after the exercise for determining the rate of heart beat deceleration or recovery, over time. Heart beat rate data of the person tested is compared with similar heart beat rate data in the memory of the computer, which data is categorized in classes of persons, and the comparison is translated into an evaluation of heart fitness.

Although a preferred embodiment of the invention has been shown and described and modifications and alternates suggested, other changes and modifications, as will become apparent to those skilled in the art, may be made without departing from the spirit of the invention.

What is claimed is:

1. Apparatus for evaluating the fitness of the heart of a person, said apparatus including:
   (a) means, adapted to be operable by said person, for selecting sex data and age data, individual to said person, from a plurality of sex data and age data, for classifying said person among other persons on the basis of sex and age;
   (b) means for instructing said person in a format of an exercise designed to increase a beat rate of said person's heart;
   (c) exercise means for engagement by said person for changing said beat rate of said heart, said exercise means including exercise pace detecting means for monitoring the pace at which said person is performing said exercise while said person is engaged in said exercise and exercise pace control means for communicating to said person instructions flow slow-up or slow-down or maintain constant the pace at which said exercise is being performed for maintaining said pace at a predetermined pace;
   (d) means for monitoring said heart after said person performs said exercise for determining a recovery rate of said heart from an increased beat rate toward a slower beat rate; and
   (e) means for comparing said recovery rate of said person's heart with heart beat recovery rates of persons in the same classification as said person for evaluating the fitness of said heart of said person.

2. Apparatus for evaluating the fitness of the heart as in claim 1 and in which said means for selecting sex data and age data includes:
   (a) means for communicating to said person at least a first question and at least first and second answers to said first question; and
   (b) means operable by said person for selecting one answer from said first and second answers to said first question and for communicating a selected answer to said apparatus.

3. Apparatus for evaluating the fitness of the heart of a person, said apparatus including:
   (a) means, adapted to be operable by said person, for selecting a sex data and an age data, individual to aid person from a plurality of sex data and a plurality of age data for classifying said person among other persons on the basis of sex and age;
   (b) means for instructing said person in a format of an exercise designed to increase a beat rate of said person's heart;
   (c) exercise means for engagement by said person for changing said beat rate of said heart and for monitoring a pace at which said person is performing said exercise while said person is engaged in said exercise and for maintaining said pace at which said person performs said exercise at a predetermined pace;
   (d) means for monitoring said heart after said person performs said exercise for determining a recovery rate of said heart from an increased beat rate toward a slower beat rate;
   (e) means for comparing said recovery rate of said person's heart with heart beat recovery rates of persons in the same classification as said person for evaluating the fitness of said heart of said person; and
   (f) said means for selecting a sex data and an age data includes means for communicating to said person at least a first question, a second question and a third question each question followed by at least two answers respectively and means, adapted to be operated by said person, for selecting one answer from said at least two answers for each question respectively, and for communicating the answers so selected for each question to said apparatus for use in classifying said person in said classification of persons.

4. Apparatus for evaluating the fitness of the heart as in claim 3 and in which said means for monitoring further includes means for processing said electric impulses into digital pulses having characteristics which correspond to characteristics which correspond to characteristics of said electric impulses and said means for processing said electric impulses includes;
   (a) means for receiving said electric impulses in analog form;
   (b) a first filter for filtering out relatively high frequencies in said electric impulses;
   (c) a first amplifier for amplifying the filtered signal;
   (d) a second filter for further filtering out relatively high frequencies in the amplified, filtered signal;
   (e) means for rectifying said amplified filtered signal for providing a full wave rectified signal;
   (f) an integrator circuit, a peak detector circuit, and a comparator circuit each connected for receiving said full wave rectified signal as a first input, respectively, said integrator circuit providing a first output to said peak detector as second input thereto, and a summing circuit, said summing circuit connected for receiving said first output of said integrator circuit as one input and connected for receiving a second output from said peak detector as another input, said summing circuit for providing a third output applied to said comparator circuit as a second input thereto: and, (g) a timer connected for receiving a fourth output from said comparator circuit, said timer for providing a timed digital signal having a frequency corresponding to the passed low frequencies of said filtered signal.

5. Apparatus for evaluating the fitness of the heart of a person as in claim 3 and in which said exercise means for engagement by said person includes:

dual step means each step of said dual step positioned at a level whereby said person need step up in order to stand on each respective step of said dual step means;

means coupled to each step of said dual step means for indicating when said person is standing on each said step respectively; and means for monitoring said means for indicating and determining the pace at which said person steps up on to a surface of said dual step means and steps down from said surface of said dual step means.

6. Apparatus for evaluating the fitness of the heart as in claim 5 and in which said exercise means further includes means for indicating to said person that said person should speed up the pace at which said person is stepping up on said step means and stepping down from said step means, if said pace is slower than said predetermined pace and for indicating to said person that said person should slow down the pace at which said person is stepping up on said step means and stepping down from said step means if said pace is faster than said predetermined pace.

7. A method of evaluating the fitness of the heart of a person including the steps of:

(a) classifying the person whose heart fitness is being evaluated on the basis of sex and age characteristics as provided by said person for categorizing said person in a class of persons of similar sex and age characteristics;

(b) instruction said person to exercise by stepping up on and stepping off from a step means and monitoring each step up and each step down for determining the pace of the person so exercising;

(c) instructing said person to increase the speed of exercise if said pace is too slow or to decrease the speed of exercise if said pace is too fast as compared to a predetermined pace;

(d) timing the duration of exercise so that said person exercises for a predetermined time;

(e) instructing said person to grasp a set of electrodes means with said hands for sensing electric impulses in said hands related to said heart beat functions for determining the heart beat rate of said heart after said person having exercised under controlled conditions;

(f) determining the recovery rate of said heart beat over a timed interval;

(g) comparing the determined recovery rate of said heart beat with recovery rates of heart beat of persons in the same classification as said person tested;

(h) translating the comparison made in terms of heart condition; and (i) displaying such results.

8. A method of evaluating the fitness of the heart of a person as in claim 7 and in which the step (a) includes the steps of:

(aa) communicating a question to said person to be answered by said person; and (ab) communicating at least two answers to said question and instructing said person to indicate the desired answer from said at least two answers.

9. A method of evaluating the fitness of the heart of a person as in claim 7 and in which step c also includes playing an audible rhythm with an audio means to said person while said person is exercising for helping said person to maintain said predetermined pace of said exercise.

10. Apparatus for evaluating the fitness of the heart of a person, said apparatus including:

(a) means adapted to be operated by said person, for selecting a sex data and an age data from a plurality of sex data and age data for classifying said person among other persons on the basis of sex and age;

(b) means for instructing said person in a format of an exercise designed to increase a beat rate of said person's heart;

(c) exercise means for engagement by said person for changing said beat rate of said heart and for monitoring a pace at which said person is performing said exercise while said person is engaged in said exercise and for maintaining said pace at which said person performs said exercise at a predetermined pace;

(d) means for monitoring said heart after said person performs said exercise for determining a recovery rate of said heart from an increased beat rate toward a slower beat rate, said means for monitoring including a first electrode and a second electrode, each adapted to be grasped by a hand, for sensing and receiving electric impulses representing functions of the heart of said person, said electric impulses having characteristics which represent characteristics of said functions; and, (e) means for comparing said recovery rate of said person's heart with heart beat recovery rates of persons in the same classification as said person for evaluating the fitness of said heart of said person.

* * * * *

UNITED STATES PATENT AND TRADEMARK OFFICE
CERTIFICATE OF CORRECTION

PATENT NO. : 4,898,182

DATED : February 6, 1990

INVENTOR(S) : Brian Hawkins, et al

It is certified that error appears in the above-identified patent and that said Letters Patent is hereby corrected as shown below:

On the title page, the illustrative Figure should be deleted to appear as shown. After, item [76] the following should be inserted: [73] Assignee:

--Body Log, Inc.
    Armonk, N.Y.--

The sheets of Drawings consisting of Figures 1-4 should be deleted to appear as per attached sheets.

Signed and Sealed this

Twenty-third Day of April, 1991

*Attest:*

HARRY F. MANBECK, JR.

*Attesting Officer*     *Commissioner of Patents and Trademarks*

United States Patent [19]

Hawkins et al.

[11] Patent Number: 4,898,182

[45] Date of Patent: Feb. 6, 1990

[54] APPARATUS FOR EVALUATING HEART FITNESS

[76] Inventors: Brian Hawkins, 8 MacDonald Ave.; Jerald Greenberg, 34 Maple Ave.; Ofer Alon, 6 MacDonald Ave., all of Armonk, N.Y. 10504; Victor Marten, 144-45, 41 Ave., Apt. 3S, Flushing, N.Y. 11355; Edward Banyai, 133 Woodland Ave., New Rochelle, N.Y. 10805; Jennifer A. Edwards, 8 MacDonald Ave., Armonk, N.Y. 10504; David M. Banyai, 133 Woodland Ave., New Rochelle, N.Y. 10805; Juan C. Sanchez; Eran Sitnik, both of 137 Old Kisco Rd., Armonk, N.Y. 10504; Joseph A. Yozzo, 17 Lawrence St., Mt. Kisco, N.Y. 10549

[21] Appl. No.: 152,113

[22] Filed: Feb. 4, 1988

[51] Int. Cl.⁴ .............................................. A61B 5/04
[52] U.S. Cl. ................................... 128/707; 128/709; 128/696
[58] Field of Search ............... 128/707, 709, 695, 696; 272/69

[56] References Cited

U.S. PATENT DOCUMENTS

| | | | |
|---|---|---|---|
| 3,518,985 | 7/1970 | Quinton | 128/707 |
| 3,675,640 | 7/1972 | Gatts | 128/671 |
| 4,278,095 | 7/1981 | Lapeyre | 272/69 |
| 4,281,663 | 8/1981 | Pringle | 128/689 |
| 4,319,581 | 3/1982 | Cutter | 128/707 |
| 4,367,752 | 1/1983 | Jimenez et al. | 128/707 |
| 4,566,461 | 1/1986 | Lubell et al. | 128/707 |
| 4,708,337 | 11/1987 | Shyu | 272/69 |

OTHER PUBLICATIONS

Biosig, Inc., INSTA-PULSE heart rate monitor sales brochure, Print date 9/78, BioSig Inc., P.O. Box 651, NDG, Montreal, Quebec, H4A 3R1, Canada.

Primary Examiner—Francis Jaworski
Assistant Examiner—George Manuel
Attorney, Agent, or Firm—Stephen E. Feldman

[57] ABSTRACT

A heart fitness evaluation system is set up in booth form in which a participating person may have the fitness condition of his heart evaluated based on a step test protocol. Personalized data is transmitted to the system in the form of selected answers to questions proposed, and the person is classified according to such data provided for the purposes of data comparison. The person engages in supervised exercise over a timed period to accelerate heart functions. After the activity, the person's heart is monitored to determine the recovery rate of the heart over real time. Comparison of the recovery rate is made against stored physiological data relating to heart rate recovery of classified persons, which is translated in to the fitness level of the person's heart and displaying such results.

10 Claims, 4 Drawing Sheets